(12) United States Patent
Fratini et al.

(10) Patent No.: US 7,763,324 B2
(45) Date of Patent: Jul. 27, 2010

(54) TEXTILE AND FOOTWEAR PRODUCTS TREATED WITH SULFUR

(75) Inventors: Marcello Fratini, Grosseto (IT); Paolo Salinaro, Florence (IT)

(73) Assignee: Sicem Industriale S.p.A., Florence (IT)

( * ) Notice: Subject to any disclaimer, the term of this patent is extended or adjusted under 35 U.S.C. 154(b) by 1055 days.

(21) Appl. No.: 10/577,602

(22) PCT Filed: Feb. 12, 2004

(86) PCT No.: PCT/IT2004/000054

§ 371 (c)(1),
(2), (4) Date: Apr. 27, 2006

(87) PCT Pub. No.: WO2005/041913

PCT Pub. Date: May 12, 2005

(65) Prior Publication Data

US 2007/0036672 A1     Feb. 15, 2007

(51) Int. Cl.
*B05D 1/18* (2006.01)
*D06B 3/00* (2006.01)

(52) U.S. Cl. .............. 427/430.1; 427/434.2; 427/434.6; 28/154

(58) Field of Classification Search ............... 427/430.1, 427/2.1
See application file for complete search history.

(56) References Cited

U.S. PATENT DOCUMENTS

| 4,260,660 | A | * | 4/1981 | McCarter | .................... 442/136 |
| 6,077,794 | A | * | 6/2000 | Tabata et al. | ................ 442/123 |

FOREIGN PATENT DOCUMENTS

| BR | 9903830 | 4/2001 |
| JP | 60233016 | 11/1985 |
| JP | 09217274 | 8/1997 |
| JP | 09285483 | 11/1997 |
| JP | 09285483 A * | 11/1997 |
| WO | WO 03094881 | 11/2005 |

OTHER PUBLICATIONS

Ewing et al. Sulphur-Impregnated Clothing to Protect Against Chiggers. Journal of Economic Entomology. vol. 18. Dec. 1925, 827-829.*

* cited by examiner

*Primary Examiner*—David Turocy
(74) *Attorney, Agent, or Firm*—Pollack, P.C.

(57) ABSTRACT

A composition for inhibiting noxious odors of a user's foot. The composition comprises an active ingredient of elemental sulfur, preferably in a micronized state, applied to an article to be deodorized, such as socks, stockings or other textile or footwear article intended to come into direct or indirect contact with the user's foot. The active ingredient may be combined with other substances in an effort to achieve stable adherence to the article and, thereby, provide lasting release of the active ingredient over time, even after subsequent cleaning of the article.

11 Claims, No Drawings

TEXTILE AND FOOTWEAR PRODUCTS TREATED WITH SULFUR

FIELD OF THE INVENTION

The present invention relates generally to chemical treatment of articles and, more particularly, to a composition for suppression or elimination of noxious odors and its application to textiles, footwear articles, sanitary products and/or the like.

BACKGROUND OF THE INVENTION

It is well-known that human feet can often emanate noxious odors when footwear, for example, shoes, are removed, especially after being worn for an entire day. This phenomena, it has been found, is even more noticeable with shoes made of a material, such as a synthetic or rubber, that prevents transpiration of foot perspiration during use. After prolonged use, the shoes frequently becomes impregnated with offensive odors and they too become a source of such odors.

Presently, there is no truly effective remedy for the annoyance and inconvenience of foot odors. Indeed, of the products available on the market, none achieve more than slight attenuation of noxious foot odors. In other words, use of conventional products have yielded no significant improvement in odor reduction. The age-old problem of noxious foot odor, therefore, remains, without solution.

Research has shown that the noxious odors emitted by human feet are caused by particular type of fungus, commonly known as *Tinea Pedis*, that proliferates in anaerobic environments, particularly in the interstices between the third, fourth and fifth toe. That this is the least exposed and aired area of the foot, combined with the normal body temperature conditions (equal to about 37° C.) characteristic of a person's foot, provides a habitat that is optimal for fungal growth. In turn, the fungus readily takes root and resists humidity both from sweating and upon washing of the user's feet.

As sweating of the foot increases or intensifies, so does the degree of humidity and, in turn, proliferation of *Tinea Pedis* and the noxious odors that result. The intensity of sweating that occurs during footwear use depends not only on the predisposition of the person, but also on the type of shoe being worn. It is conventional wisdom, for example, that sport shoes have a tendency to hinder transpiration. The particularly abundant sweating and, hence, moisture that results, together with the anaerobic environment and body temperature conditions of the foot, it has been found, are particularly favorable for the proliferation of *Tinea Pedis*.

OBJECTS AND SUMMARY OF THE INVENTION

Accordingly, it is an object of the present invention to provide a composition and a method that are effective in neutralizing entirely the proliferation of odiferous fungi and, therefore, completely eliminating noxious odors often characteristic of sweating feet.

It is another object of the present invention to provide a composition suitable for ready application to and/or impregnation of socks, stockings, or another textile or footwear article coming into contact—directly or indirectly—with a portion of the user's foot to be deodorized, so as to achieve stable, persistent and lasting odor suppression, even after successive washings of the article.

According to one aspect of the present invention, there is provided a method of treating, or partially or wholly impregnating, a textile and/or footwear article to be worn on, or associated with, a user's foot with an active deodorizing ingredient which comprises elemental sulphur, or a composition capable of liberating elemental sulphur. Initially, the article is treated or impregnated with a selected composition having, in addition to the active ingredient, a polymeric binder for providing stable adherence of the active ingredient to the article and gradual release therefrom over time. The polymeric binder is preferably a selected acrylic, silicone, butadiene or polyurethane resin. The active ingredient and resin are distributed in an aqueous bath in which the article is immersed. The active ingredient has a concentration in the aqueous bath between about 0.3 g/l and about 1.0 g/l, and the resin is a selected silicon resin having a concentration between about 10 g/l and about 20 g/l. The aqueous bath further comprises a selected cationic surfactant and a selected softener at concentrations between about 10 g/l, and about 20 g/l, and about 2 g/l and about 5 g/l, respectively.

In accordance with another aspect of the present invention, a composition is provided for partially or integrally treating a textile and/or footwear article to be worn on, or associated with, a user's foot. The composition has an active deodorizing ingredient which comprises elemental sulphur or a mixture capable of liberating elemental sulphur. The article includes, in addition to the active ingredient, a selected polymeric binder for providing stable adherence of the active ingredient to the article and gradual release therefrom over time. The polymeric binder is preferably a selected acrylic, silicone, butadiene or polyurethane resin. The active ingredient and the resin are distributed in an aqueous bath in which the article is immersed. The active ingredient has a concentration between about 0.3 g/l and about 1.0 g/l. The resin is a selected silicon resin and has a concentration between about 10 g/l and about 20 g/l. The aqueous bath further comprises a selected cationic surfactant and a selected softener having concentrations of between about 10 g/l and about 20 g/l, and about 2 g/l and about 5 g/l, respectively.

According to a further aspect of the present invention, there is provided a composition for partially or integrally treating a textile and/or article to be worn on, or associated with, a user's foot. The composition has an active deodorizing ingredient that includes elemental sulphur or a mixture capable of liberating elemental sulphur. The composition comprises, in addition to the active ingredient, a selected polymeric binder for providing stable adherence of the active ingredient to the article and gradual release therefrom over time. The polymeric binder is desirably a selected acrylic, silicone, butadiene or polyurethane resin. The active ingredient and the resin are distributed in an aqueous bath in which the article is immersed. The active ingredient has a concentration between about 5 g/l and about 10 g/l and is emulsified with a selected non-ionic surfactant. The resin is a selected emulsified acrylic resin and has a concentration between about 3 g/l and about 5 g/l. The bath, in the case of a wool-based article, has a pH at least slightly acidic using acetic acid or, in the case of an article with a cellulose base, a relatively neutral pH.

In accordance with yet another aspect of the present invention, a textile and/or footwear article is provided that is integrally or partially impregnated or treated with a composition having an active deodorizing ingredient which comprises elemental sulphur or a mixture capable of liberating elemental sulphur, the article being treated or impregnated with such composition. The composition comprises, in addition to the active ingredient, a selected polymeric binder for providing stable adherence of the active ingredient to the article and gradual release therefrom over time. It is preferred that the polymeric binder be a selected acrylic, silicone, butadiene or polyurethane resin, and that the active ingredient and resin be distributed in an aqueous bath in which the article is immersed. The active ingredient has a concentration in the aqueous bath between about 0.3 g/l and about 1.0 g/l. The resin is a selected silicon resin and has a concentration between about 10 g/l and about 20 g/l. The aqueous bath further comprises a selected cationic surfactant and a selected softener at concentrations between about 10 g/l and about 20 g/l, and about 2 g/l and about 5 g/l, respectively.

DETAILED DESCRIPTION OF THE PREFERRED EMBODIMENTS

Referring now to further particulars of the present invention, there is provided a specific, illustrative deodorizing composition and method for treating an article to come into direct or indirect contact with a user's foot, such articles including, but not limited to socks, stockings, insoles, soles and uppers of shoes, so as to yield footwear articles that do not acquire an unpleasant odor during use. According to various aspects of the present invention, such treatment is preferably carried out by the manufacturer of the article before it is brought to market and, in the case of soles, uppers or other parts of shoes, before or during production of the shoe.

The following is an example of a preferred deodorizing composition, according to one aspect of the present invention, for applying a preferred active principle or ingredient to a pair of socks. More specifically, the composition includes an aqueous solution containing the following:

- about 0.2g/l to about 0.3 of wettable elemental sulphur (i.e., the active principle), preferably in micronized form;
- about 10 g/l to about 20 g/l of resin, for example, a silicon resin;
- about 10 g/l to about 20 g/l of a cationic surfactant, e.g., a common fixative for dyes;
- about 2 g/l to about 5 g/l of softener, such as a perfumed Henkel® softener.

Desirably, the socks to be treated are immersed for a few minutes in a bath prepared as set forth above. With socks made of a fibrous material containing wool, for instance, it is preferred that the bath be brought to a temperature of about 40° C. In the case of other materials, the temperature of the bath is increased to about 90° C. Those skilled in the art will appreciate, however, that not only the treatment time and temperature, but also the formulation of the composition, may be varied selectively according to the particular machine employed. Generally speaking, the parameters described above are considered to be optimal in the case of treatment using, for example, a centrifugal washing machine. Treatment is then completed with a brief phase of rinsing, drying and centrifuging, this once again at a temperature that may be varied according to the type of textile fiber employed. Moreover, immersion in such an aqueous bath may be replaced by a treatment phase in which the composition is sprayed directly onto the articles using a conventional ejection device.

Alternatively or concurrently, the active ingredient is applied prior to actual manufacture of the articles of clothing such as footwear articles, i.e., to fabrics from which the articles are to be made. This may be accomplished, for example, through continuous operation using a foulard machine with a bath comprising about 5 g/l to about 10 g/l of active ingredient in emulsified form having a selected non-ionic surfactant, about 3 g/l to about 5 g/l of emulsified acrylic resin, in a pH made slightly acidic using acetic acid (pH=5) in the case of wool-based fabrics, or with a neutral pH for fabrics having a cellulose base. Following a step of wringing the fabric, the fabric is preferably dried in a "Rameuse" machine at a temperature of at least about 150° C., which is considered necessary to assure polymerization of the acrylic resin.

In general, the resin portion of the composition described above fundamentally operates to fix or adhere the active ingredient to a textile fiber, the fiber holding and/or being impregnated with the ingredient and, thus, making it resistant to subsequent washings. In a micronized state, the elemental sulphur is released from the composition very slowly, thereby assuring its deodorizing action over the course of time. Neither the silicon resin nor the acrylic resin cause any appreciable alteration in softness characteristics of the fiber, making them particularly suitable for the purpose intended. Optionally, other types of resins may be utilized, for instance, resins with a butadiene base, even if combined in appropriate proportions.

When applying the composition to materials having a woolen base, it is preferable to use resins, such as those with radical-type polymerization mechanisms, that are capable of being polymerized at low temperatures. In any case, the softener may serve to attenuate a possible stiffening effect due to the presence of a resin. The surfactant, in turn, aids in increasing the fixing power of elemental sulphur to the fibrous material.

The present invention has been found particularly advantageous for application to textile fibers, for example, typically in accordance with the modalities described above, because it insures optimal effectiveness of the deodorizing action without altering either the appearance or the original softness of the supporting materials, which also remain completely free of odor. Alternatively or concurrently, this application, may be accomplished by various modes of operation, especially by variation in the material for which it is intended and, therefore, also the machines that are employed. For instance, so-called "Dutch machines" could be utilized, whereby movement of the bath is more gentle and thus avoids physical alteration of materials made of wool fibers.

As indicated previously, another beneficial use of the present invention contemplates application of a sulphur-based composition directly to shoes, namely, through treatment according to one of the above-described modalities, of the textile lining of an insole intended to come into contact with the user's foot. Further in the alternative or concurrently therewith, the elemental sulphur is mixed with a selected glue often employed for securing a textile lining of the shoe to the base material (generally a polyurethane) of the shoe insole.

In the art of cleaning and disinfection, a deodorizing cream for local use can readily be obtained by amalgamating the elemental sulphur, or a substance having an elemental sulphur base, with vaseline or lanoline in proportions appropriate for obtaining the required density and homogeneity. According to a typical composition, for example, about 3% by weight elemental sulphur, the sulphur is mixed with vaseline and lanoline in equal percentages. Deodorizing properties may also be applied to swathing strips and elastic bandages, in accordance with one of the methods described above for fixing the active ingredient to textile materials.

Overall, socks, or other articles associated with a user's foot, treated in accordance with the present invention, render a user's foot entirely free of noxious odors, even after a day of extensive activity wearing sport shoes. Experiments conducted on feet wearing treated socks, with user's particularly prone to foot odors, resulted in complete eradication of noxious foot odors. Repeated washings of the socks did not result in any noticeable loss or decay in deodorizing properties. Moreover, no allergic reaction of any kind were experienced by any of the users.

It shall be understood by those skilled in the art that the specific procedures and applications underlying the preferred embodiments, as set forth herein, are not intended to limit the present invention. Generally speaking, the invention includes the identification of an active ingredient that is not only capable of inhibiting the proliferation of fungus, e.g., *Tinea Pedis*, that causes noxious foot odor, but also eliminates such odors completely, even when the foot remains encased in a shoe for an entire day, without any adverse effects to the wearer as to allergic reaction or other intolerance. It is also considered noteworthy that the active ingredient of interest, namely, elemental sulphur, apart from being inert, does not interact with sebaceous secretions and is, therefore, absolutely tolerable from both a hygienic and sanitary standpoint.

Although the present invention has been described in connection with any use of elemental sulphur for deodorizing a user's feet, those skilled in the art will appreciate that application can be made to other textile products such as yarns, cloths of various compositions, stockings, socks, footwear articles, and the like, giving consideration to the purpose for which the invention is intended.

Various modifications and alterations may be appreciated based on a review of this disclosure. These changes and additions are intended to be within the scope and spirit of the invention as defined by the following claims.

What is claimed is:

1. A method of treating, or partially or wholly impregnating, a textile and/or footwear article to be worn on, or associated with, a user's foot with an active deodorizing ingredient which comprises elemental sulphur, or a composition comprising elemental sulphur and is capable of liberating elemental sulphur, the method including the steps of:
    treating or impregnating the article with a selected composition having, in addition to the active ingredient, a polymeric binder for providing stable adherence of the active ingredient to the article and gradual release therefrom over time, the polymeric binder being a selected acrylic, silicone, butadiene or polyurethane resin, and the active ingredient and resin being distributed in an aqueous bath in which the article is immersed, wherein the active ingredient has a concentration in the aqueous bath between about 0.3 g/l and about 1.0 g/l, the resin is a selected silicon resin having a concentration between about 10 g/l and about 20 g/l, and the aqueous bath further comprises a selected cationic surfactant and a selected softener at concentrations between about 10 g/l and about 20 g/l and about 2 g/l and about 5 g/l, respectively.

2. The method set forth in claim 1, wherein the polymeric binder is a selected acrylic, silicone, butadiene or polyurethane resin, the active ingredient and the resin being distributed in a non-aqueous composition with which the article is applied or impregnated.

3. The method set forth in claim 1, wherein the aqueous bath is brought to a temperature of at least about 40° C.

4. The method set forth in claim 1 wherein the active ingredient has a concentration between about 5 g/l and about 10 g/l and is emulsified with a non-ionic surfactant, the resin being a selected emulsified acrylic resin and having a concentration between about 3 g/l and about 5 g/l, the bath, in the case of a wool-based article, having a pH at least slightly acidic using acetic acid or, in the case of an article with a cellulose base, a relatively neutral pH.

5. The method set forth in claim 1 wherein the textile products articles, subsequent to immersion in the bath, is wrung and dried at a temperature of at least about 150° C. in order to polymerize the acrylic resin.

6. The method set forth in claim 1, wherein the polymeric binder is a selected adhesive utilized for assembling a shoe or a part thereof.

7. The method set forth in claim 1 wherein the active ingredient is a selected wettable micronized sulphur.

8. A composition for partially or integrally treating a textile and/or footwear article to be worn on, or associated with, a user's foot, the composition having an active deodorizing ingredient which comprises elemental sulphur or a mixture comprising elemental sulphur and is capable of liberating elemental sulphur, wherein the article comprises, in addition to the active ingredient, a selected polymeric binder for providing stable adherence of the active ingredient to the article and gradual release therefrom over time, wherein the polymeric binder is a selected acrylic, silicone, butadiene or polyurethane resin, the active ingredient and the resin being distributed in an aqueous bath in which the article is immersed, and the active ingredient has a concentration between about 0.3 g/l and about 1.0 g/l, the resin being a selected silicon resin and having a concentration between about 10 g/l and about 20 g/l, the aqueous bath further comprising a selected cationic surfactant and a selected softener having concentrations of between about 10 g/l and about 20 g/l, and about 2 g/l and about 5 g/l, respectively.

9. The composition set forth in claim 8, wherein the active ingredient is a selected wettable micronized sulphur.

10. A composition for partially or integrally treating a textile and/or article to be worn on, or associated with, a user's foot, the composition having an active deodorizing ingredient that includes elemental sulphur or a mixture comprising elemental sulphur and is capable of liberating elemental sulphur, wherein the composition comprises, in addition to the active ingredient, a selected polymeric binder for providing stable adherence of the active ingredient to the article and gradual release therefrom over time, wherein the polymeric binder is a selected acrylic, silicone, butadiene or polyurethane resin, the active ingredient and the resin being distributed in an aqueous bath in which the article is immersed, and the active ingredient has a concentration between about 5 g/l and about 10 g/l and is emulsified with a selected non-ionic surfactant, the resin being a selected emulsified acrylic resin and having a concentration between about 3 g/l and about 5 g/l, the bath, in the case of a wool-based article, having a pH at least slightly acidic using acetic acid or, in the case of an article with a cellulose base, a relatively neutral pH.

11. A textile and/or footwear article integrally or partially impregnated or treated with a composition having an active deodorizing ingredient which comprises elemental sulphur or a mixture comprising elemental sulphur and is capable of liberating elemental sulphur, wherein the article is treated or impregnated with such composition, the composition comprising, in addition to the active ingredient, a selected polymeric binder for providing stable adherence of the active ingredient to the prod-net article and gradual release therefrom over time, the polymeric binder being a selected acrylic, silicone, butadiene or polyurethane resin, and the active ingredient and resin being distributed in an aqueous bath in which the article is immersed, wherein the active ingredient has a concentration in the aqueous bath between about 0.3 g/l and about 1.0 g/l, the resin is a selected silicon resin and having a concentration between about 10 g/l and about 20 g/l, and the aqueous bath further comprises a selected cationic surfactant and a selected softener at concentrations between about 10 g/l and about 20 g/l, and about 2 g/l and about 5 g/l, respectively.

* * * * *